United States Patent [19]

Mattison

[11] 4,065,455
[45] Dec. 27, 1977

[54] 5-HALOGEN-SUBSTITUTED 7 ALKYL AND 7-ALKENYL 8-HYDROXYQUINOLINES

[75] Inventor: Phillip L. Mattison, New Brighton, Minn.

[73] Assignee: General Mills Chemicals, Inc., Minneapolis, Minn.

[21] Appl. No.: 447,629

[22] Filed: Mar. 4, 1974

[51] Int. Cl.² ........................................... C07D 215/24
[52] U.S. Cl. .................... 260/289 XA; 423/DIG. 14; 423/24
[58] Field of Search ..................... 260/289 R, 289 XA

[56] References Cited

U.S. PATENT DOCUMENTS 2,178,571  11/1939  Fletts ........................... 260/289 R X
3,637,711  3/1968  Budde et al. ..................... 260/289 R

OTHER PUBLICATIONS

Fiedler, "Arch. Pharm", v.293, pp. 609–621 (1960) as abstracted in Chem. Abstracts, vol. 54, Abst. No. 24744 (1960).
Hollingshead, "Analyst", vol. 80, pp. 729–735, (1955).
Beleher et al., "New Methods of Analytical Chemistry" pp. 257–262, Reinhold (1964).
Takamoto et al., "Analytical Chem", 1965, pp. 1249–1251.

Primary Examiner—Donald G. Daus
Assistant Examiner—D. B. Springer
Attorney, Agent, or Firm—Gene O. Enockson; Patrick J. Span

[57] ABSTRACT

Compounds of the structure

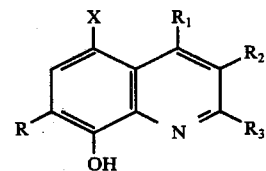

where X is Cl or Br, R is a branched chain alkyl or alkenylradical containing about 8 to 20 carbon atoms and $R_1$, $R_2$ and $R_3$ are hydrogen or alkyl groups of 1 to 4 carbon atoms. The new compounds find use in extraction of metals.

14 Claims, No Drawings

5-HALOGEN-SUBSTITUTED 7 ALKYL AND 7-ALKENYL 8-HYDROXYQUINOLINES

The present invention relates to certain new halogen-substituted 8-hydroxyquinolines. These compounds find use as reagents for the liquid ion exchange extraction of some metals, especially copper or zinc.

The compounds of the invention have the structure

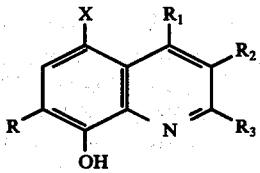

where X is Cl or Br, R is a branched chain alkyl or alkenyl radical containing about 8 to 20 carbon atoms and $R_1$, $R_2$ and $R_3$ are hydrogen or lower alkyl groups of 1 to 4 carbon atoms. R is preferably an alkenyl radical of 12 or more carbon atoms. Preferably at least two of the groups $R_1$, $R_2$ and $R_3$ are hydrogen and when one of the same is alkyl, such group is preferably methyl.

The 7-alkenyl substituted compounds may be prepared by reacting 5-chloro (or bromo) -8-hydroxyquinoline with an alkenyl chloride in the presence of sodium hydroxide and dimethylsulfoxide with subsequent heating. The 7-alkyl substituted compounds are desirably prepared by reacting 8-hydroxyquinoline with an alkenyl chloride in the presence of sodium hydroxide and the dimethylsulfoxide solvent (heating to rearrange as above). The product is then hydrogenated and chlorinated or brominated. The compounds wherein $R_1$, $R_2$, or $R_3$ are alkyl are desirably prepared by reacting 2-amino-4-chloro (or bromo) phenol with an α, β-unsaturated aldehyde in the presence of 2-nitro-4-chloro (or bromo) phenol, ferrous sulfate and sulfuric acid. Such $R_1$, $R_2$, or $R_3$ substituted 5-chloro (or bromo)-8-hydroxyquinoline is then reacted as above with an alkenyl chloride.

The details of these reactions are further set forth in the examples to follow, such examples illustrating preferred embodiments without being limiting.

EXAMPLE I

Five hundred ml. dimethyl sulfoxide, 179 gm. (1.0 mole) 5-chloro-8-hydroxyquinoline, 40 gm. sodium hydroxide and 243 gm. (1.2 mole) dodecenyl chloride (5,5,7,7-tetramethyl-1-chloro-2-octene available from Rohn & Haas) were combined with stirring in that order in a one liter round bottom flask. Stirring was continued overnight at 70° C. (18 hr.). Five hundred ml. H₂O and 500 ml. Skellysolve B (a normal hexane solvent) were added and the mixture shaken. The aqueous layer was extracted with another 250 ml. Skellysolve B. The total organic layer was washed to pH 5 with water and then with about ½ liter Claisen's alkali (in portions). It was again washed with H₂O until neutral and then with aqueous NaCl and dried. The product was stripped of solvent to yield 369.3 gm. of a dark oil. Of this amount, 365.3 gm. was distilled through a one foot Vigreaux column. A 231.8 gm. fraction distilling off between 160°–170° C. at 0.06 mm Hg consisted in excess of 97% of 5-chloro-7-dodecenyl-8-hydroxyquinoline having the structure:

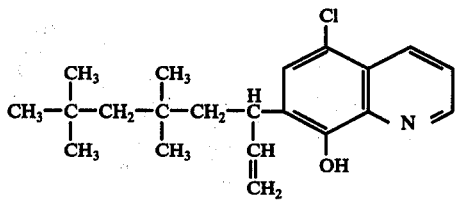

EXAMPLE II

Part A

Preparation of 7-dodecenyl-8-hydroxyquinoline.

One hundred forty five grams (1.0 mole) 8-hydroxyquinoline, 40 gm. sodium hydroxide, 500 ml. methanol and 5 gm. potassium iodide were combined in a two liter round bottom flask. To this was added 243 gm. dodecenyl chloride (as used in Example I) and the mixture stirred under reflux overnight. The product was filtered, taken up in ether and washed with 500 ml. Claisen's alkali (in five portions). The ether solution was washed several times with water until neutral, dried and the solvent stripped to yield 317.9 gm. of crude product. Of this amount, 310.9 gm. was distilled through a one foot Vigreaux after being heated in the pot to 230° C. and cooled to about 100° C. The fractions coming off at 197°–202° C., 0.7 mm. Hg. (51.1 gm.) and 202°–231° C., 0.8 mm. Hg. (96.8 gm.) consisted almost entirely of 7-dodecenyl-8-hydroxyquinoline.

Part B

Hydrogenation of 7-dodecenyl-8-hydroxyquinoline.

Ten grams 7-dodecenyl-8-hydroxyquinoline were dissolved in 90 ml. 95% ethanol and 0.1 gm. hydrogenation catalyst (Palladium on carbon) was added. This was charged to a Paar Bomb which was degassed and charged to 35 psig with H₂. The pressure fell to 14 psig in 16 min. and was then repressurized to 29 psig. Over 1½ hours this fell to 19.5 psig. The reactor was degassed at aspirator vacuum, N₂ bled in and the mixture filtered giving a plum purple solution. Solvent stripping left 9.0 gm. of product which was a dark oil. Infrared analysis showed the product to be 7-dodecyl-8-hydroxyquinoline.

Part C

Chlorination of 7-dodecyl-8-hydroxyquinoline.

Forty five grams (0.144 mole) 7-dodecyl-8-hydroxyquinoline prepared as in Part B was dissolved in 180 ml. methanol (absolute) at 25° C. and then 12.8 gm. Cl₂ (0.180 mole) was bubbled in over ½ hr. at 21°–25° C. with good stirring. Stirring was continued 50 min. and the solvent stripped on a rotary evaporator. The residue was taken up in ether and washed with H₂O to pH 5, dried and the ether stripped. The residue weighed 46.3 gm. of which 43 gm. was recrystallized from absolute ethanol giving 24.5 gm. of gold colored platelets (m.p. 88.5°–90° C.). The product was 5-chloro-7-dodecyl-8-hydroxyquinoline having the structure:

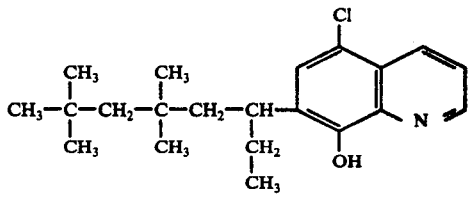

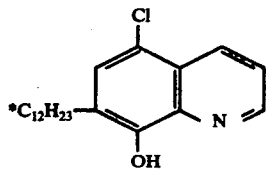

*Same comment as Example IV above, but with tetrapropylene.

EXAMPLE III

To 5.0 gm. 7-dodecyl-8-hydroxyquinoline as prepared in Part B of Example II dissolved in 12 ml. methanol was added 2.56 gm. Br$_2$ over a ten minute period at 25°–30° C. with stirring. The solution was stirred for an additional hour at 25° C. and was then taken up in ether and washed with water to pH 5. The product solution was further washed with saturated aqueous NaCl, dried and the ether stripped to give 6.0 gm. of a brown solid. The 5-bromo-7-dodecyl-8-hydroxyquinoline had the structure:

EXAMPLE VI

Example IV was essentially repeated using diisobutenyl chloride in place of the indicated dodecenyl chloride of Example I. The diisobutenyl chloride was prepared as follows: Into the reaction flask was charged 1000 g. (8.91 mole) of diisobutylene. The flask was heated to 95° C. and the Cl$_2$ (566 gm., 7.98 mole) was added over 5 hours at 95°–100° C. The product was then distilled through a 1 ft. Vigreaux column. The product had the following structure:

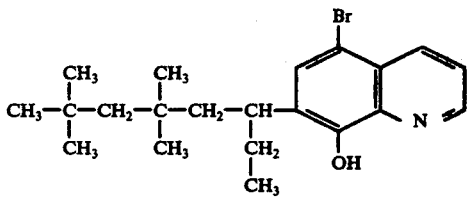

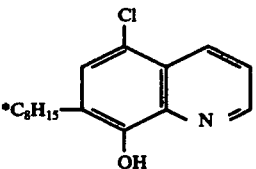

*Similar reasons as in Examples IV and V above.

EXAMPLE IV

Example I was essentially repeated using triisobutenyl chloride in place of the indicated dodecenyl chloride. The triisobutenyl chloride was prepared as follows. To a two liter, three neck round bottom flask equipped with a stirrer, dry ice condenser and a gas inlet tube was charged 700 g. (4.16 mole) triisobutylene (available from Eastman Kodak). The flask was heated to 95° C. and 266 gm. (3.75 mole) Cl$_2$ was added over 1¼ hr. at 95°–105° C. The reaction mixture was cooled overnight and then distilled through a 1 ft. Vigreaux column. The product obtained from the triisobutylene chloride had the structure:

EXAMPLE VII

Into a one liter, three neck round bottom flask fitted with a stirrer, condenser and thermometer were charged 72 gm. (0.5 mole) 2-amino-4-chlorophenol, 43.4 gm. (0.25 mole) 2-nitro-4-chlorophenol, 5 gm. ferrous sulfate and 70 ml. sulfuric acid (conc.). This mixture was heated to 140° C., the thermometer was replaced with an addition funnel and 112 gm. (1.6 mole) methacrolein was added dropwise over 40 min. so as to maintain moderate reflux (initial temp. 140° C., 80° C. at completion of addition). The reaction mixture was refluxed for four hours, water was added and excess 2-nitro-4-chlorophenol was steam distilled off. The solids recovered from the neutralized (50% KOH solution followed by saturated Na$_2$CO$_3$) pot residue were dissolved in 1.4 liter of methanol and filtered to remove insoluble tars. After stripping the methanol, the residue was extracted with hot 10% HCl, filtered to remove solids, and the solids were twice treated with hot acid. The combined acid solutions were washed twice with chloroform, neutralized (KOH—Na$_2$CO$_3$ solutions as above) and the resulting precipitate was filtered off and air-dried. This material was dissolved in ether, filtered and evaporated to give 15.7 g. of crude product. Crystallization of a portion from ether—petroleum ether gave white needles, m.p. 125°–127° C.

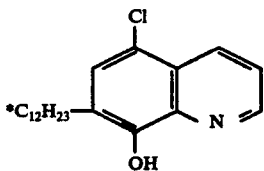

*The C$_{12}$H$_{23}$ radical is highly branched, the exact nature of the branching being dependent on the particular starting material (isobutylene) and conditions of its manufacture.

EXAMPLE V

Example IV was essentially repeated using tetrapropenyl chloride in place of the indicated dodecenyl chloride of Example I. The tetrapropenyl chloride was prepared as follows: Into the reaction flask was charged 1000 gm. (5.98 mole) tetrapropylene (available from Enjay Chemical). The flask was heated to 95° C. and 377 gm. (5.37 mole) Cl$_2$ was added over three hours at 95°–100° C. The product was distilled through a 1 ft. Vigreaux column. The product had the structure:

The procedure of Example I was essentially repeated using 15.7 gm. (0.08 mole) 3-methyl-5-chloro-8-hydroxyquinoline as above prepared in place of the 5-chloro-8-hydroxyquinoline and 20 gm. of dodecenyl chloride. The product, 3-methyl-5-chloro-7-dodecenyl-8-hydroxyquinoline had the structure:

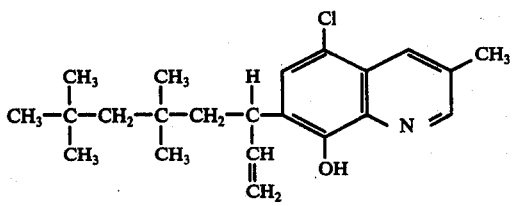

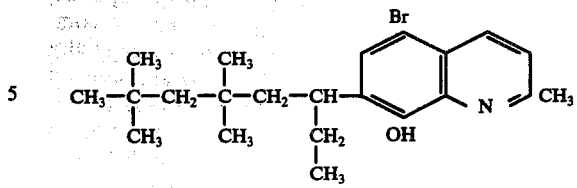

EXAMPLE VIII

Example I was essentially repeated using 2-methyl-8-hydroxyquinoline in place of 5-chloro-8-hydroxyquinoline. The resultant 2-methyl-7-dodecenyl-8-hydroxyquinoline was hydrogenated by the procedure of Example II, Part B to give 2-methyl-7-dodecyl-8-hydroxyquinoline.

Chlorination: A stirred suspension of 23.7 g. (0.073 mole) of 2-methyl-7-dodecyl-8-hydroxyquinoline in 100 ml. of methanol was maintained at 0°–5° C. during the addition of a solution of 5.3 g. (0.074 mole) of $Cl_2$ in 100 ml. of methanol over 5–10 min. After addition was complete, the mixture was stirred at 0° C. for 1 hr., then at room temperature overnight.

The mixture was poured into an ice-cold $NaHCO_3$ solution (final aq. pH 7–8) and extracted with ether. The extract was washed with water, dried over $MgSO_4$, filtered and evaporated to give 19.8 g. of product containing

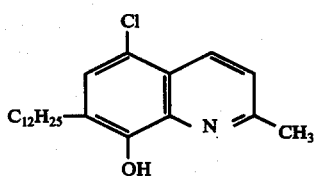

plus a carbonyl-containing impurity (probably

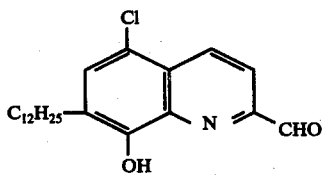

A mixture of the crude product, 10 g. of Girard's P reagent (acetohydrazide pyridinium chloride) and 10 ml. of acetic acid in 100 ml. of 95% ethanol was refluxed for 45 min., cooled, and neutralized with saturated $Na_2CO_3$ solution. After addition of water and ether extraction the extract was washed with water, dried over $MgSO_4$, filtered and evaporated to give 15.6 g. of product as a clear red oil.

EXAMPLE IX

Example VIII was essentially repeated except that $Br_2$ was used in place of $Cl_2$. The product, 2-methyl-5-bromo-7-dodecyl-8-hydroxyquinoline had the structure:

EXAMPLE X

Example VIII was essentially repeated except that 4-methyl-8-hydroxyquinoline was used in place of 2-methyl-8-hydroxyquinoline. The 4-methyl starting material was prepared as follows: In a 1 liter 3 neck round bottom flask fitted with a stirrer, thermocouple, addition funnel and reflux condenser was placed 300 g. of polyphosphoric acid. The acid was heated to 90° C. and 109 g. (1.0 mole) of o-aminophenol was added over 2.5 hrs. in 7–8 portions with vigorous stirring. After addition was complete, the mixture was stirred at 90°–100° C. for 10 min., then 105 g. (1.5 mole) of methyl vinyl ketone was added portionwise over 1.5 hrs. With each addition the temperature rose to 120°–130° C. After addition was complete, the mixture was stirred at 110° C. for 45 min., then cooled to 70° C. and 200 ml. of water was added. The mixture was stirred at room temperature for 30 min., then allowed to sit overnight.

Volatile materials were steam-distilled off and the precipitate from the neutralized residue (50% KOH followed by saturated $Na_2CO_3$ solution) was filtered, washed with water and air-dried. The dried precipitate was triturated with chloroform, filtered, and the remaining solid (o-aminophenol) was washed with chloroform.

The combined chloroform solutions were washed with water, dried over $MgSO_4$, filtered and evaporated to give 74.8 g. of crude product. Crystallization from ethanol gave 58.2 g. of light brown solid, m.p. 137°–139° C., and an additional 9.1 g. was obtained by sublimation (130°–140° C. and 0.1 mm.) of the mother liquors. The product after alkylation and hydrogenation as in Example II followed by chlorination and purification as in Example VIII had the structure:

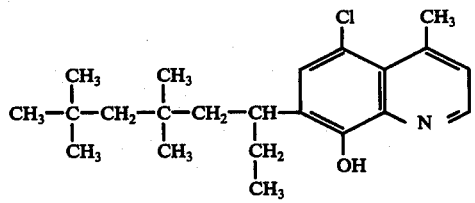

As indicated previously, the new compounds of the invention find use in the liquid ion exchange extraction of metals, particularly copper and zinc. As such, they exhibit unexpectedly low loading of acid as compared to the corresponding compounds which do not contain chlorine or bromine substitution. They improve the kinetics and/or the total amount of copper extracted when used in combination with known phenolic oximes. The copper extraction process and the combination reagent which used therein which contains the compounds of this invention disclosed and claimed in Application Ser. No. 447,594, entitled LIQUID ION EXCHANGE EXTRACTION OF COPPER USING COMBINATIONS OF 2-HYDROXYBENZO- PHENOXIMES AND SUBSTITUTED 8-HYDROXYQUINOLINES filed of even date with this application, now abandoned. The combination of the compounds with oxime extractants allows for substantially complete recovery of zinc from aqueous ammoniacal solutions thereof. The zinc recovery process is disclosed and claimed in Robert B. Sudderth and Wayne H. Jensen's Application Ser. No. 447,630 entitled LIQUID ION EXCHANGE EXTRACTION OF ZINC USING COMBINATIONS OF 2-HYDROXYBENZOPHENONE OXIMES AND 8-HYDROXYQUINOLINES also filed of even date with the present application, now abandoned.

As disclosed in the above-identified applications, the combinations of reagents are dissolved in an organic solvent preferably having a boiling point above about 150° C. and the solution is contacted with the aqueous metal containing solution to form a complex of the metal and the reagents. The organic phase is then separated from the aqueous phase and the metal values are stripped from the organic phase.

The high boiling organic solvents are essentially water immiscible and are preferably aliphatic or aromatic hydrocarbons such as the petroleum derived liquid hydrocarbons, either straight or branched, such as kerosene, fuel oil, naphtha, etc. In addition to the simple hydrocarbon solvents, chlorinated hydrocarbons may also desirably be used. Accordingly, both the unsubstituted and the chlorinated solvents are contemplated by the term "liquid hydrocarbon".

In the process of the invention, the combination reagent as described is dissolved in the organic solvent in an amount sufficient to extract at least some of the metal values from the aqueous solution thereof (normally the amount used will be less than 50% by weight based on the organic solvent). Preferably, the combination reagent will be used in amounts of about 2 to 15% by weight based on the weight of the organic solvent.

The phenolic oxime and substituted 8-hydroxyquinoline can be used in widely varying weight ratios such as 10:1 to 1:10. Preferably, however, the phenolic oxime-substituted 8-hydroxyquinoline will be used in a weight ratio of 5:1 to 1:1.

The aqueous solution containing the copper preferably has a pH below about 7.0 and the invention is of particular value when the copper containing solutions have a pH of less than about 3.0. The aqueous solution containing zinc preferably has a pH above 7.0 and the invention is of particular value when the zinc containing solutions have a pH of greater than about 7.2 up to about 10.0.

The aqueous:organic phase ratios can very widely since the contacting of any quantity of the solution of the combination reagent will result in extraction of copper values into the organic phase. However, the organic:aqueous phase ratios are preferably in the range of 20:1 to 1:20, and even more preferably 5:1 to 1:5. For practical purposes, the extractions (and stripping) are normally carried out at ambient temperatures and pressures. The entire process can be carried out continuously with the stripped organic solvent solution being recycled for contacting further quantities of metal containing solutions.

The loaded organic is preferably stripped using aqueous acid stripping mediums such as aqueous sulfuric acid (i.e. 25–100 g./l. $H_2SO_4$). The metal is then desirably recovered from the aqueous stripping medium by electrolysis. The loaded organic:aqueous stripping phase ratios can also vary widely. However, the overall object of the process is to provide a metal containing stripping solution in which the metal is sufficiently pure, is at high enough concentration, and is dissolved in a proper matrix, such that the metal may be easily recovered in a pure form. Accordingly, the loaded organic aqueous stripping phase ratio will preferably be in the range of 20:1 to 1:5.

The following data shows the utility of the compounds of the present invention as described.

EXAMPLE XI

A 4% wt./vol. solution of 3-chloro-5-nonyl-2-hydroxybenzophenoxime in Napoleum 470 (a low odor kerosene from Kerr-McGee Corp.) was made up by dissolving 40 g. of the oxime in one liter of the kerosene. The nonyl group was branched chain being derived from nonyl phenol available from Monsanto (also employed in subsequent examples). Portions of this solution were used alone or with the additions 1% wt./vol. of various substituted 8-hydroxyquinolines in kinetics studies. These extraction kinetics were determined by shaking 10 ml. of the organic solutions and 10 ml. of aqueous in a 60 ml. separatory funnel for 15 seconds. The organic phases were separated, filtered and analyzed for copper. This was repeated with fresh solutions for 30, 60, 120 and 300 seconds. The organic copper concentration was plotted versus time, and the curve extrapolated to equilibrium loading. The time at which 90% of equilibrium was reached is set forth in the Table to follow. The aqueous for the extraction runs was a 4 g./l. $Cu^{++}$ (from $CuSO_4$) aqueous solution, the pH being adjusted with concentrated $H_2SO_4$ to the initial value desired. All kinetic studies were conducted at ambient temperatures. Where a formulation did not reach 90% of equilibrium within 300 seconds, the percent that was reached at 300 seconds is given—i.e. 63%/300 seconds.

Table A

| Run No. | Organic | | Time to 90% Equilibrium Extraction. Sec. | |
|---|---|---|---|---|
| | Conc. Wt./vol.% | Reagent | pH 0.9 | pH 0.3 |
| 1 | 4 | 3-chloro-5-nonyl-2-hydroxybenzophenoxime (hereinafter phenolic oxime) | 40%/300 | 15%/300 |
| 2 | 4 | phenolic oxime | | |
| | 1 | 7-octenyl-8-hydroxyquinoline | ppt. | 100 |
| 3 | 4 | phenolic oxime | | |
| | 1 | 7-diisobutenyl-8-hydroxyquinoline | 21 | 36 |
| 4 | 4 | phenolic oxime | | |
| | 1 | 7-triisobutenyl-8-hydroxyquinoline | 180 | 225 |
| 5 | 4 | phenolic oxime | | |
| | 1 | 7-dodecenyl*-8-hydroxyquinoline | 45 | 80 |
| 6 | 4 | phenolic oxime | 83%/300 | 48%/300 |
| | 1 | 2-butyl-7-dodecenyl*-8-hydroxyquinoline | | |
| 7 | 4 | phenolic oxime | | |

Table A-continued

| Run No. | Organic Conc. Wt./vol.% | Reagent | Time to 90% Equilibrium Extraction. Sec. | |
|---|---|---|---|---|
| | | | pH 0.9 | pH 0.3 |
| | 1 | 7-dodecyl**-8-hydroxyquinoline | 144 | 199 |
| 8 | 4 | phenolic oxime | 86%/300 | 83%/300 |
| | 1 | **5-chloro-7-dodecyl-8-hydroxyquinoline | | |
| 9 | 4 | phenolic oxime | | |
| | 1 | 5-chloro-7-dodecenyl*-8-hydroxyquinoline | 110 | 128 |
| 10 | 4 | phenolic oxime | | |
| | 1 | 5-bromo-7-dodecyl**-8-hydroxyquinoline | 194 | 188 |

*dodecenyl is 5,5,7,7-tetramethyl-1-octene-3-yl (also used in subsequent examples)
**saturated dodecenyl* (also used in subsequent examples)

EXAMPLE XII

Acid loading was measured by shaking 30 ml. of various of the organic solutions as used in Example XI for two minutes with 10 ml. of 300 g./l. $H_2SO_4$ in water. The organic phases were separated, filtered and then 25 ml. of each organic phase was shaken for two minutes with 10 ml. water. The resulting aqueous phase was separated, filtered and titrated for acid. The concentration of acid in the organic phases was then back calculated, the results being set forth in the following Table B:

Table B

| Organic as in Run No. (of Table I) | Acid Loading $H_2SO_4$, g./l. |
|---|---|
| 3 | 7.7 |
| 4 | 3.5 |
| 5 | 5.0 |
| 6 | 3.8 |
| 7 | 4.4 |
| 8 | 0.45 |
| 9 | 0.2 |
| 10 | 0.2 |

EXAMPLE XIII

Stripping kinetics were studied by first loading the organic phase by contacting it two times with equal volumes of 4 g./l. $Cu^{++}$ (from $CuSO_4$), pH 1.90 aqueous solution.

The loaded organics were then stripped as follows: 10 ml. portions of the loaded organic were contacted with 10 ml. of 20 g./l. $Cu^{++}$ (from $CuSO_4$) 300 g./l. $H_2SO_4$ for 15, 30, 60, 120, 300 sec. each in 60 ml. separatory funnels. The organic phases were filtered and analyzed for $[Cu^{++}]$ and the results were plotted as in Example XI. Such results are set forth in Table C which follows:

Table C

| Loaded Organic Starting Organic As In Run No. (of Table A) | Time to 90% Equilibrium Stripping (Sec.) |
|---|---|
| 1 | 23%/300 |
| 2 | ppt. |
| 3 | 127 |
| 4 | 140 |
| 5 | 20 |
| 6 | 30 |
| 7 | 26 |
| 8 | 83%/300 |
| 9 | 58 |
| 10 | 142 |

The best system reported in Examples XI to XIII is the combination of the phenolic oxime and 5-chloro-7-dodecenyl-8-hydroxyquinoline. Such system is stable, loads very little acid and gives quite good kinetics.

EXAMPLE XIV

The $pH_{\frac{1}{2}}$ of various of the phenolic oxime-substituted 8-hydroxyquinoline systems was determined as follows: Organic solutions of the reagent or combinations of reagents were equilibrated with aqueous copper solutions giving a range of final, equilibrium pH's. The aqueous solutions contained copper in large excess so that the aqueous copper level remained essentially constant for all samples. This gave pH isotherms, where organic copper concentrations were plotted against pH. The organic loading reaches a maximum at high pH. The pH at which half of maximum loading is reached is taken as the $pH_{\frac{1}{2}}$.

The isotherms were obtained using 10 ml. samples of solutions of the reagents in a high aromatic naphtha (HAN available from Esso). The aqueous phases consisted of 5 ml. 20 g./l. Cu (as $CuSO_4$) and 5 ml. of pH adjusting solutions. These mixtures were mechanically shaken for 17 hours at 25° C. and the phases separated, filtered and analyzed for copper. The final pH was also measured. The results are set forth in the following Tables.

Table D-1

Organic Solution - 1% wt./vol. 5-chloro-7-dodecenyl-8-hydroxyquinoline

| pH Adjusting Solution | $H_2O$ ml. | pH (final) | $Cu^{++}$ Org. g./l. |
|---|---|---|---|
| 5 ml. 2M $H_2SO_4$ | 0 | 0.04 | 0.29 |
| 3 ml. 2M $H_2SO_4$ | 2 | 0.30 | 0.45 |
| 5 ml. 1M $H_2SO_4$ | 0 | 0.41 | 0.50 |
| 3 ml. 1M $H_2SO_4$ | 2 | 0.60 | 0.62 |
| 1 ml. 1M $H_2SO_4$ | 4 | 1.07 | 0.78 |
| 0.5 ml. 1M $H_2SO_4$ | 4.5 | 1.38 | 0.83 |
| — | 5 | 1.87 | 0.85 |
| 0.5 ml. .5M $NaHCO_3$ | 4.5 | 4.10 | 0.89 |

Table D-2

Organic Solution - 1% wt./vol. 5-nonyl-2-hydroxybenzophenoxime

| pH Adjusting Solution | $H_2O$ ml. | pH (final) | $Cu^{++}$ Org. g./l. |
|---|---|---|---|
| 5 ml. 2M $H_2SO_4$ | 0 | 0.09 | 0.00 |
| 3 ml. 2M $H_2SO_4$ | 2 | 0.34 | 0.02 |
| 5 ml. 1M $H_2SO_4$ | 0 | 0.44 | 0.02 |
| 3 ml. 1M $H_2SO_4$ | 2 | 0.67 | 0.06 |
| 1 ml. 1M $H_2SO_4$ | 4 | 1.18 | 0.28 |
| 0.5 ml. 1M $H_2SO_4$ | 4.5 | 1.43 | 0.43 |
| — | 5 | 2.22 | 0.64 |
| 0.5 ml. 0.5M $NaHCO_3$ | 4.5 | 4.41 | 0.72 |

Table D-3

Organic Solution - 1% wt./vol. 3-chloro-5-nonyl-2-hydroxybenzophenoxime

| pH Adjusting Solution | $H_2O$ ml. | pH (final) | $Cu^{++}$ Org. g./l. |
|---|---|---|---|
| 5 ml. 2M $H_2SO_4$ | 0 | 0.16 | 0.33 |
| 3 ml. 2M $H_2SO_4$ | 2 | 0.24 | 0.48 |
| 5 ml. 1M $H_2SO_4$ | 0 | 0.33 | 0.52 |
| 3 ml. 1M $H_2SO_4$ | 2 | 0.70 | 0.57 |
| 1 ml. 1M $H_2SO_4$ | 4 | 1.10 | 0.63 |

Table D-3-continued

Organic Solution - 1% wt./vol. 3-chloro-5-nonyl-2-hydroxy-benzophenoxime

| pH Adjusting Solution | $H_2O$ ml. | pH (final) | $Cu^{++}$ Org. g./l. |
|---|---|---|---|
| 0.5 ml. 1M $H_2SO_4$ | 4.5 | 1.43 | 0.63 |
| — | 5 | 2.25 | 0.67 |
| 0.5 ml. 0.5M $NaHCO_3$ | 4.5 | 4.21 | 0.70 |

Table D-4

Organic Solution - 1% wt./vol. 5-chloro-7-dodecenyl-8-hydroxyquinolien and 1% wt./vol. 5-nonyl-2-hydroxybenzophenoxime

| pH Adjusting Solution | $H_2O$ ml. | pH (final) | $Cu^{++}$ Org. g./l. |
|---|---|---|---|
| 5 ml. 2M $H_2SO_4$ | 0 | 0.03 | 0.34 |
| 3 ml. 2M $H_2SO_4$ | 2 | 0.26 | 0.52 |
| 5 ml. 1M $H_2SO_4$ | 0 | 0.35 | 0.58 |
| 3 ml. 1M $H_2SO_4$ | 2 | 0.57 | 0.77 |
| 1 ml. 1M $H_2SO_4$ | 4 | 1.05 | 1.10 |
| 0.5 ml. 1M $H_2SO_4$ | 4.5 | 1.29 | 1.26 |
| — | 5 | 1.84 | 1.48 |
| 0.5 ml. 0.5M $NaHCO_3$ | 4.5 | 2.20 | 1.55 |

Table D-5

Organic Solution - 1% wt./vol. 5-chloro-7-dodecenyl-8-hydroxyquinoline and 1% wt./vol. 3-chloro-5-nonyl-2-hydroxybenzophenoxime

| pH Adjusting Solution | $H_2O$ ml. | pH (final) | $Cu^{++}$ Org. g./l. |
|---|---|---|---|
| 5 ml. 2M $H_2SO_4$ | 0 | 0.00 | 0.77 |
| 3 ml. 2M $H_2SO_4$ | 2 | 0.26 | 1.03 |
| 5 ml. 1M $H_2SO_4$ | 0 | 0.35 | 1.09 |
| 3 ml. 1M $H_2SO_4$ | 2 | 0.57 | 1.24 |
| 1 ml. 1M $H_2SO_4$ | 4 | 1.04 | 1.44 |
| 0.5 ml. 1M $H_2SO_4$ | 4.5 | 1.31 | 1.47 |
| — | 5 | 1.77 | 1.50 |
| 0.5 ml. 0.5M $NaHCO_3$ | 4.5 | 2.17 | 1.58 |

Table D-6

Organic Solution - 1% wt./vol. of each of 5-chloro-7-dodecenyl-8-hydroxyquinoline, 5-nonyl-2-hydroxybenzo-phenoxime and 3-chloro-5-nonyl-2-hydroxybenzophenoxime

| pH Adjusting Solution | $H_2O$ ml. | pH (final) | $Cu^{++}$ Org. g./l. |
|---|---|---|---|
| 5 ml. 2M $H_2SO_4$ | 0 | 0.00 | 0.79 |
| 3 ml. 2M $H_2SO_4$ | 2 | 0.21 | 1.13 |
| 5 ml. 1M $H_2SO_4$ | 0 | 0.29 | 1.23 |
| 3 ml. 1M $H_2SO_4$ | 2 | 0.55 | 1.47 |
| 1 ml. 1M $H_2SO_4$ | 4 | 0.97 | 1.83 |
| 0.5 ml. 1M $H_2SO_4$ | 4.5 | 1.16 | 1.96 |
| — | 5 | 1.63 | 2.16 |
| 0.5 ml. 0.5M $NaHCO_3$ | 4.5 | 1.86 | 2.20 |

The $pH_i$ values based on the above experimental values are as follows:

Table D-7

| Systems | $pH_i$ |
|---|---|
| Table D-1 | 0.32 |
| Table D-2 | 1.34 |
| Table D-3 | 0.15 |
| Table D-4 | 0.64[1] |
| Table D-5 | 0.03[1] |
| Table D-6 | 0.24[1] |

[1] The $pH_i$ calculated for these combination reagents from the plots of the individual compounds alone is 0.78, 0.20, 0.52, respectively.

EXAMPLE XV

A 11.3% wt./vol. solution of an oxime extractant in Napoleum 470 (a low odor kerosene from Kerr McGee Corp.) was prepared by dissolving 180 g. of 2-hydroxy-5-nonylbenzophenoxime and 5.4 g. of 5,8-diethyl-7-hydroxydodecane-6-oxime in 1 liter of the kerosene. Portions of this solution were used alone or with additions of various substituted 8-hydroxyquinolines at various concentrations to study solubilities therein of a zinc-reagent complex. The studies were conducted by contacting 10 ml. of the reagent solution 5 times with an equal volume of an aqueous ammoniacal solution containing zinc at a level of 12 g./l. the aqueous solution having a pH of 7.6. This resulted in the reagent being completely loaded with zinc which solutions were then observed for precipitation over a period of 2–3 days. A summary of the data is given in the following Table E.

TABLE E

| Compound | wt/vol % Compound | [Zn] ORG | Observation | wt/vol % Compound | [Zn] ORG | Observation | wt/vol % Compound | Observation |
|---|---|---|---|---|---|---|---|---|
| 5-chloro-7-dodecencyl-8-hydroxyquinoline | 1 | 6.01 g/l | No ppt. | 1.5 | 7.47 | Very slight ppt. | 2.5 | Small Amount ppt. |
| 5-chloro-7-octenyl-8-hydroxyquinoline | 1 | 6.37 | Very Slight ppt. | 1.5 | 8.00 | Very slight ppt. | 2.5 | Slight Amount ppt. |
| 3-Methyl-5-chloro-7-dodecenyl-8-hydroxyquinoline | 1 | 6.52 | Very slight ppt. | 1.5 | 8.15 | Very slight ppt. | 2.5 | Small Amount ppt. |
| 2-Methyl-5-bromo-7-dodecyl-8-hydroxyquinoline | 1 | 6.31 | Very slight ppt. | 1.5 | 8.30 | Large Amount ppt. | — | — |
| 2-Methyl-5-chloro-7-dodecyl-8-hydroxyquinoline | 1 | | Very slight ppt. | 1.5 | | Slight ppt. | 2.5 | Large Amount ppt. |
| 5-Chloro-7-dodecyl-8-hydroxyquinoline | 1 | | Very slight ppt. | 1.5 | | Slight ppt. | 2.5 | Large Amount ppt. |
| Blank (11.3 oxime solution only) | — | 5.03 | No ppt. | | | | | |

EXAMPLE XVI

The zinc minimum raffinate was studied by contacting the extractant reagent with the same aqueous zinc solution at an organic to aqueous ratio O/A of 20:1 and 5:1 for two minutes and determining the amount of zinc in the aqueous raffinate. The aqueous zinc containing solution and the oxime extractant solution were the same as in Example XV. The quinoline compounds were at a level of 0.0247M. The data in the following Table F summarizes the zinc minimum raffinate values.

TABLE F

Zinc Minimum Raffinate

| Compound | [Zn] g/l Aq. | |
|---|---|---|
| | O/A=20 | O/A=5 |
| Blank (oxime extractant solution only) | 1.08 | 4.80 |
| 5-chloro-7-dodecenyl-8-hydroxyquinoline | 0.0097 | 2.53 |
| 5-chloro-7-dodecyl-8-hydroxyquinoline | 0.0082 | 2.76 |
| 5-chloro-7-octenyl-8-hydroxyquinoline | 0.0043 | 2.50 |
| 5-bromo-7-dodecyl-8-hydroxyquinoline | 0.0036 | 2.60 |
| 3-methyl-5-chloro-7-dodecenyl-8-hydroxyquinoline | 0.0029 | 2.48 |
| 2-methyl-5-chloro-7-dodecyl-8-hydroxyquinoline | 0.221 | 3.28 |
| 2-methyl-5-bromo-7-dodecyl-8-hydroxyquinoline | 0.203 | 3.12 |
| 7-dodecenyl-8-hydroxyquinoline | 0.0075 | 2.58 |

EXAMPLE XVII

Extraction isotherms were run using 5-chloro-7-dodecyl-8-hydroxyquinoline, the oximes extractant of Example XV, mixture thereof, and with 7-dodecenyl-8-hydroxyquinoline. These extractions were conducted at various organic to aqueous ratios by shaking the organic solution and aqueous solution in a separatory funnel for 60 minutes, after which the phases were separated and analyzed for zinc. The results can be seen from the following Tables.

TABLE G-1

Extraction Isotherm on 11.3% wt/vol oxime extractant alone with aqueous solution having 12 g/l Zn. and a pH of 7.8

| O/A | [Zn] ORG, g/l | [Zn] Aq, g/l |
|---|---|---|
| 1/2 | 3.93 | 10.5 |
| 1/1 | 3.17 | 9.10 |
| 2/1 | 2.42 | 7.80 |
| 5/1 | 1.45 | 4.78 |
| 10/1 | 1.01 | 1.96 |
| 20/1 | 0.55 | 0.93 |

TABLE G-2

Extraction Isotherm on same solution as in G-1 with 0.85% of 5-chloro-7-dodecyl-8-hydroxyquinoline using aqueous solution having 12 g/l Zn. and a pH of 7.6

| O/A | [Zn] ORG, g/l | [Zn] Aq, g/l |
|---|---|---|
| 1/2 | 4.94 | 10.5 |
| 1/1 | 4.10 | 8.33 |
| 2/1 | 3.18 | 6.27 |
| 6/1 | 1.81 | 1.72 |
| 10/1 | 1.26 | 0.19 |
| 20/1 | 0.61 | 0.0015 |

TABLE G-3

Extraction Isotherm on same reagent combination as in G-2 but using an aqueous solution having 12.7 g/l and a pH of 7.6

| O/A | *[Zn] ORG, g/l | [Zn] Aq, g/l |
|---|---|---|
| 1/2 | 5.4 | 10.0 |
| 1/1 | 4.3 | 8.40 |
| 2/1 | 3.3 | 6.20 |
| 5/1 | 2.0 | 2.55 |
| 10/1 | 1.2 | 0.27 |
| 20/1 | 0.6 | 0.004 |

*Calculated from the Aqueous analyses

TABLE G-4

Extraction Isotherm on 1% wt/vol of 5-chloro-7-dodecyl-8-hydroxyquinoline alone in the kerosene and an aqueous solution having 2 g/l Zn. and a pH of 7.6

| O/A | [Zn] ORG, g/l | [Zn] Aq, g/l |
|---|---|---|
| 1/2 | 0.694 | 1.65 |
| 1/1 | 0.681 | 1.33 |
| 2/1 | 0.590 | 0.90 |
| 6/1 | 0.304 | 0.28 |
| 10/1 | 0.196 | 0.16 |
| 20/1 | 0.101 | 0.08 |

TABLE G-5

Extraction Isotherm 1% 7-dodecenyl-8-hydroxyquinoline alone in the kerosene and an aqueous solution having 2 g/l Zn. and a pH of 7.6

| O/A | [Zn] ORG, g/l | [Zn] Aq, g/l |
|---|---|---|
| 1/2 | 0.777 | 1.70 |
| 1/1 | 0.718 | 1.31 |
| 2/1 | 0.623 | 0.89 |
| 6/1 | 0.308 | 0.29 |
| 10/1 | 0.199 | 0.16 |
| 20/1 | 0.104 | 0.077 |

EXAMPLE XVIII

The amount of acid loaded by the oxime extractant alone and in combination with other compounds was determined using kerosene (Napoleum 470) or the organic solvent at the wt./vol. percent indicated in the table below. The procedure consisted of contacting 30 ml. of organic solution with 10 ml. of 160 g/l. $H_2SO_4$ for 2 minutes. The phases were separated and 25 ml. of filtered organic was shaken for 2 minutes with 10 ml. of distilled water. The aqueous phase was then titrated with standard base in order to determine the acid concentration. A summary of the data collected is in Table H.

TABLE H

Acid Loading

| Compound | [Acid] ORG, g/l |
|---|---|
| 27% the oxime extractant of Example I above | 0.08 |
| 27% oxime extractant of Example I with 0.85% 5-chloro-7-dodecyl-8-hydroxyquinoline | 0.24 |
| 27% oxime extractant of Example I with 0.85% 7-dodecenyl-8-hydroxyquinoline | 1.40 |

EXAMPLE XIX

Extraction isotherms were run at various O/A ratios on organic solution of 0.295M 5-chloro-7-dodecenyl-8-hydroxyquinoline and 0.295M 7-dodecenyl-8-hydroxyquinoline in perchloroethylene. Both compounds were precontacted with 160 g/l $H_2SO_4$ and filtered through filter paper before being contacted with an aqueous ammoniacal solution having 12 g/l Zn and a pH of 7.6. (The 7-dodecenyl-8-hydroxyquinoline gave some third phase formation.) The tables below summarize the extraction isotherm data on the acid loaded reagents.

TABLE J-1

Extraction Isotherm on 0.295M 5-chloro-7-dodecenyl-8-hydroxyquinoline

| O/A | *[Zn] ORG, g/l | [Zn] Aq, g/l |
|---|---|---|
| 1/4 | 10.8 | 10.0 |
| 1/1 | 8.80 | 3.90 |
| 2/1 | 6.02 | 0.66 |
| 5/1 | 2.52 | 0.11 |

TABLE J-1-continued

Extraction Isotherm on 0.295M 5-chloro-7-dodecenyl-8-hydroxyquinoline

| O/A | *[Zn] ORG, g/l | [Zn] Aq, g/l |
|---|---|---|
| 10/1 | 1.26 | 0.044 |
| 20/1 | 0.63 | 0.018 |

*Calculated from the aqueous analyses

TABLE J-2

Extraction Isotherm on 0.295M 7-dodecenyl-8-hydroxyquinoline

| O/A | *[Zn] ORG, g/l | [Zn] Aq, g/l |
|---|---|---|
| 1/4 | 10.8 | 10.0 |
| 1/1 | 8.0 | 4.68 |
| 2/1 | 5.47 | 1.75 |
| 5/1 | 2.46 | 0.39 |
| 10/1 | 1.25 | 0.17 |
| 20/1 | 0.63 | 0.075 |

*Calculated from the aqueous analyses

EXAMPLE XX

Zinc Minimum Raffinate

A number of different oximes and combinations thereof with 5-chloro-7-dodecenyl-8-hydroxyquinoline were run on the zinc minimum raffinate test which involves contacting the reagent solution in kerosene (Napoleum 470) with an aqueous solution having 12 g./l.Zn and a pH of 7.6 at an O/A of 20/1 and 5/1 for 2 minutes. The data is summarized in the following table.

TABLE K

Zinc Minimum Raffinate

| Oxime | wt./vol.% 5-chloro-7-dodecenyl-8-hydroxy quinoline | [Zn] Aq, g/l O/A=20 | [Zn] Aq, g/l O/A=5 |
|---|---|---|---|
| 11.3%, wt/vol, oxime mixture of Example XV | 0 | 1.08 | 4.80 |
| 11.3%, wt/vol, oxime mixture of Example XV | 0.85 | 0.01 | 2.53 |
| 11.9%, wt/vol* | 0 | ppct. | ppct. |
| 11.9%, wt/vol* | 0.85 | .004 | ppct. |
| 10.8%, wt/vol, 6-n-butyl-6-hydroxydodecane-5-oxime | 0 | 8.90 | 10.1 |
| 10.8%, wt/vol, 6-n-butyl-6-hydroxydodecane-5-oxime | 0.85 | 2.25 | 7.20 |
| 10.8%, wt/vol, 2-hydroxy-5-methyl-α-ethyl hexano phenone oxime | 0 | 8.10 | 9.00 |
| 10.8%, wt/vol, 2-hydroxy-5-methyl-α-ethyl hexano phenone oxime | 0.85 | 0.51 | 5.18 |
| 10.8%, wt/vol, 5,8-diethyl-7-hydroxydodecane-6-oxime | 0 | 7.95 | 10.3 |
| 10.8%, wt/vol, 5,8-diethyl-7-hydroxydodecane-6-oxime | 0.85 | 0.26 | 7.30 |
| 10.8%, wt/vol, 2-hydroxy-5-nonylbenzophenone oxime | 0 | 1.26 | 4.56 |
| 10.8%, wt/vol, 2-hydroxy-5-nonylbenzophenone oxime | 0.85 | 0.052 | 2.89 |
| None | 0.85 | 5.65 | |
|  | 0.85 | 4.78 | |

*mixture of 2-hydroxy-3-chloro-5-nonylbenzophenone oxime and 5,8-diethyl-7-hydroxydodecane-6-oxime in ratio by weight of 10:1.

EXAMPLE XXI

The zinc minimum raffinate test was conducted in the same manner as in Example XX using different quinolines. All compounds were tested in Napoleum 470 with 10.8 wt./vol.% of the oxime extractant mixture of Example XV and a level of 0.0247M quinoline compounds.

TABLE L

Zinc Minimum Raffinate

| Quinoine Compound | [Zn] Aq, g/l O/A=20 | [Zn] Aq, g/l O/A=5 |
|---|---|---|
| 4-Methyl-5-chloro-7-dodecyl-8-hydroxyquinoline | 0.0065 | 1.68 |
| 5-Chloro-7-isododecenyl-8-hydroxyquinoline (triisobutylene) | 0.0049 | 2.63 |
| 5-Chloro-7-isododecenyl-8-hydroxyquinoline (tetrapropylene) | 0.0083 | 2.28 |

EXAMPLE XXII

The various derivatives were combined at various concentrations with 10.8% wt./vol. of the oxime extractant mixture of Example XV in Napoleum 470 and contacted 5 times with equal volumes of an aqueous solution having 12 g/l Zn and a pH of 7.6. The resultant zinc loaded solutions were observed for precipitation over a period of 2–3 days. A summary of the data is given in the following tables.

TABLE M-1

4-Methyl-5-chloro-7-dodecyl-8-hydroxyquinoline

| [% "Quinoline"] | Observation |
|---|---|
| 1 | Small amount ppt. |
| 1.5 | Small amount ppt. |
| 2.5 | Large Amount ppt. |

TABLE M-2

5-Chloro-7-isododecenyl-8-hydroxyquinoline*

| [% "Quinoline"] | Observation |
|---|---|
| 1 | Small amount ppt. |
| 1.5 | Small amount ppt. |
| 2.5 | Moderate amount ppt. |

*Isododecenyl side chain was obtained from triisobutylene.

TABLE M-3

5-Chloro-7-isododecenyl-8-hydroxyquinoline*

| [% "Quinoline"] | Observation |
|---|---|
| 1 | Small amount ppt. |
| 1.5 | Moderate amount ppt. |

TABLE M-3-continued

| 5-Chloro-7-isododecenyl-8-hydroxyquinoline* | |
|---|---|
| [% "Quinoline"] | Observation |
| 2.5 | Moderate amount ppt. |

*Isododecenyl side chain was obtained form tetrapropylene.

The foregoing examples illustrate that the combination of various oximes with various 8-hydroxyquinolines provide for essentially complete extraction of zinc and provide advantages over the use of oximes or quinolines alone in the extraction of zinc as earlier discussed herein.

The embodiments of the invention in which an exclusive property or privilege is claimed are defined as follows:

1. A compound of the formula:

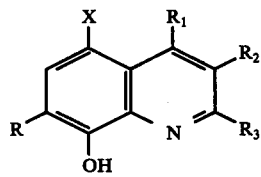

wherein X is Cl or Br, R is a branched chain alkenyl radical of about 8 to 20 carbon atoms obtained by reaction of a starting 8-hydroxyquinoline compound with a 1-chloro-1-alkene and $R_1$, $R_2$ and $R_3$ are hydrogen or alkyl groups of 1 to 4 carbon atoms with the proviso that at least two of $R_1$, $R_2$ and $R_3$ are hydrogen.

2. A compound as defined in claim 1 in which R is an alkenyl radical of 12 to 20 carbon atoms.

3. A compound as defined in claim 2 in which one of $R_1$, $R_2$ and $R_3$ is methyl.

4. A compound as defined in claim 2 in which the 1-chloro-2-alkene is obtained from triisobutylene.

5. A compound as defined in claim 4 in which X is Cl and $R_1$, $R_2$ and $R_3$ are hydrogen.

6. A compound as defined in claim 2 in which the 1-chloro-2-alkene is obtained from tetrapropylene.

7. A compound as defined in claim 6 in which X is Cl and $R_1$, $R_2$ and $R_3$ are hydrogen.

8. A compound of the formula:

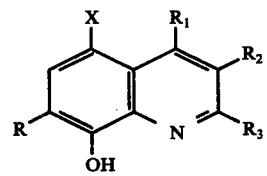

where X is Cl or Br, R is a branched chain alkyl radical of about 8 to 20 carbon atoms obtained by reaction of a starting 8-hydroxyquinoline compound with a 1-chloro-2-alkene followed by hydrogenation of the resulting alkenyl group and $R_1$, $R_2$ and $R_3$ are hydrogen or alkyl groups of 1 to 4 carbon atoms with the proviso that at least two of $R_1$, $R_2$ and $R_3$ are hydrogen.

9. A compound as defined in claim 8 in which R is dodecyl.

10. The compound 5-chloro-7-dodecenyl-8-hydroxyquinoline having the structure:

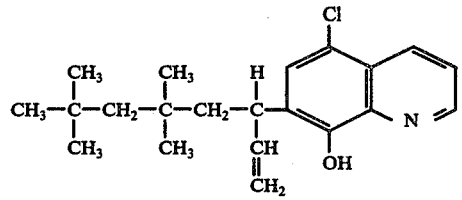

11. The compound 5-chloro-7-dodecyl-8-hydroxyquinoline having the structure:

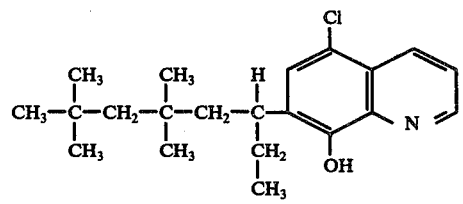

12. The compound 5-bromo-7-dodecyl-8-hydroxyquinoline having the structure:

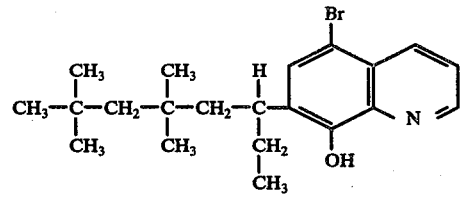

13. The compound 2-methyl-5-bromo-7-dodecyl-8-hydroxyquinoline having the structure:

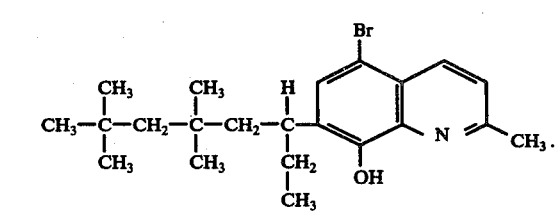

14. The compound 4-methyl-5-chloro-7-dodecyl-8-hydroxyquinoline having the structure:

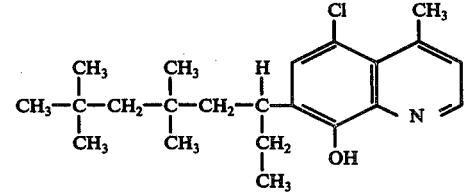

* * * * *

UNITED STATES PATENT AND TRADEMARK OFFICE
CERTIFICATE OF CORRECTION

PATENT NO. : 4,065,455
DATED : Dec. 27, 1977
INVENTOR(S) : Phillip L. Mattison

It is certified that error appears in the above-identified patent and that said Letters Patent are hereby corrected as shown below:

In the References Cited: "Beleher" should read - Belcher -

Column 2, line 40, "0.1 gm." should read - 1.0 gm. -

Column 5, line 50, after the formula, there should be a - ). -

Column 7, line 52, "very" should read - vary -

Columns 9 & 10, Table A-continued, Run No. 8, second line, "**" should be after - dodecyl -

Column 17, line 30, in claim 1, "1-chloro-1-alkene" should read - 1-chloro-2-alkene -

Signed and Sealed this

Thirteenth Day of June 1978

[SEAL]

Attest:

RUTH C. MASON
Attesting Officer

DONALD W. BANNER
Commissioner of Patents and Trademarks